United States Patent
Flower et al.

(10) Patent No.: US 11,369,762 B2
(45) Date of Patent: Jun. 28, 2022

(54) METHODS AND APPARATUS FOR ASSESSING SLEEP QUALITY

(71) Applicant: ResMed Pty Ltd, Bella Vista (AU)

(72) Inventors: Renee Frances Flower, Sydney (AU); Philip Rodney Kwok, Sydney (AU); Muditha Pradeep Dantanarayana, Sydney (AU); Ron Richard, Escondido, CA (US)

(73) Assignee: ResMed Pty Ltd, Bella Vista (AU)

(*) Notice: Subject to any disclaimer, the term of this patent is extended or adjusted under 35 U.S.C. 154(b) by 374 days.

(21) Appl. No.: 16/385,893

(22) Filed: Apr. 16, 2019

(65) Prior Publication Data

US 2019/0298948 A1     Oct. 3, 2019

Related U.S. Application Data

(63) Continuation of application No. 14/085,327, filed on Nov. 20, 2013, now Pat. No. 10,300,230, which is a
(Continued)

(30) Foreign Application Priority Data

Sep. 27, 2006 (AU) ................................ 2006905343

(51) Int. Cl.
*A61B 5/00* (2006.01)
*A61M 16/00* (2006.01)
(Continued)

(52) U.S. Cl.
CPC ......... *A61M 16/0057* (2013.01); *A61B 5/024* (2013.01); *A61B 5/369* (2021.01);
(Continued)

(58) Field of Classification Search
None
See application file for complete search history.

(56) References Cited

U.S. PATENT DOCUMENTS 5,999,846 A * 12/1999 Pardey ................. A61B 5/4812
600/544
6,091,973 A * 7/2000 Colla ................... A61B 5/0205
600/324

(Continued)

FOREIGN PATENT DOCUMENTS

| | | |
|---|---|---|
| EP | 0773504 | 5/1997 |
| WO | 1995/000001 | 1/1995 |
| WO | 2006/008743 | 1/2006 |

OTHER PUBLICATIONS

International Search Report for PCT/AU2007/00144, dated Nov. 9, 2007.
Written Opinion for PCT/AU2007/00144, dated Nov. 9, 2007.

*Primary Examiner* — Shirley X Jian
(74) *Attorney, Agent, or Firm* — Nixon & Vanderhye P.C.

(57) ABSTRACT

Systems and/or methods for assessing the sleep quality of a patient in a sleep session are provided. Data is collected from the patient and/or physician including, for example, sleep session data in the form of one or more physiological parameters of the patient indicative of the patient's sleep quality during the sleep session, a subjective evaluation of sleep quality, etc.; patient profile data; etc. A sleep quality index algorithm, which optionally may be an adaptive algorithm, is applied, taking into account some or all of the collected data. Sleep quality data may be presented to at least the patient, and it may be displayed in any suitable format (e.g., a format useful for the patient to be appraised on the progress of the treatment, a format useful for a sleep clinician to monitor progress and/or assess the effectiveness of differing treatment regimens, etc).

20 Claims, 4 Drawing Sheets

Related U.S. Application Data continuation of application No. 12/311,361, filed as application No. PCT/AU2007/001440 on Sep. 27, 2007, now Pat. No. 8,617,068.

(51) Int. Cl.
  *A61B 5/369* (2021.01)
  *A61B 5/024* (2006.01)

(52) U.S. Cl.
  CPC .......... *A61B 5/4812* (2013.01); *A61B 5/4815* (2013.01); *A61M 16/0051* (2013.01); *A61M 16/024* (2017.08); *A61M 2205/3375* (2013.01); *A61M 2205/502* (2013.01); *A61M 2205/52* (2013.01); *A61M 2230/10* (2013.01); *A61M 2230/18* (2013.01); *A61M 2230/205* (2013.01); *A61M 2230/63* (2013.01)

(56) References Cited

U.S. PATENT DOCUMENTS

| | | | |
|---|---|---|---|
| 6,120,441 A | 9/2000 | Griebel | |
| 6,468,234 B1 | 10/2002 | Van der Loos | |
| 6,878,121 B2 | 4/2005 | Krausman et al. | |
| 7,089,936 B2* | 8/2006 | Madaus | A61M 16/026 128/204.23 |
| 7,468,040 B2 | 12/2008 | Hartley | |
| 7,469,697 B2 | 12/2008 | Lee | |
| 7,524,279 B2 | 4/2009 | Auphan | |
| 7,532,934 B2 | 5/2009 | Lee | |
| 7,562,659 B2 | 7/2009 | Matarasso | |
| 7,610,094 B2 | 10/2009 | Stahmann | |
| 7,668,591 B2 | 2/2010 | Lee | |
| 7,717,112 B2 | 5/2010 | Sun | |
| 7,720,541 B2 | 5/2010 | Stahmann | |
| 7,787,946 B2 | 8/2010 | Stahmann | |
| 7,810,497 B2 | 10/2010 | Pittman | |
| 7,967,739 B2 | 6/2011 | Auphan | |
| 8,011,365 B2 | 9/2011 | Douglas | |
| 8,069,852 B2 | 12/2011 | Burton | |
| 8,321,022 B2 | 11/2012 | Stahmann | |
| 8,617,068 B2 | 12/2013 | Doherty | |
| 8,640,697 B2 | 2/2014 | Reed | |
| 9,220,856 B2 | 12/2015 | Martin | |
| 9,223,935 B2 | 12/2015 | Heneghan | |
| 9,358,353 B2* | 6/2016 | Armitstead | A61M 16/0069 |
| 2002/0185131 A1* | 12/2002 | Madaus | A61M 16/026 128/204.26 |
| 2004/0163648 A1 | 8/2004 | Burton | |
| 2005/0039745 A1 | 2/2005 | Stahmann | |
| 2005/0042589 A1 | 2/2005 | Hatlestad | |
| 2005/0061315 A1 | 3/2005 | Lee | |
| 2005/0061319 A1 | 3/2005 | Hartley | |
| 2005/0065560 A1 | 3/2005 | Lee | |
| 2005/0076909 A1 | 4/2005 | Stahmann | |
| 2005/0081847 A1 | 4/2005 | Lee | |
| 2005/0107838 A1 | 5/2005 | Lovett | |
| 2005/0115561 A1 | 6/2005 | Stahmann | |
| 2005/0143617 A1 | 6/2005 | Auphan | |
| 2005/0188991 A1 | 9/2005 | Sun | |
| 2005/0209211 A1 | 9/2005 | Heruth | |
| 2005/0209511 A1 | 9/2005 | Heruth | |
| 2005/0209513 A1 | 9/2005 | Heruth | |
| 2005/0217674 A1* | 10/2005 | Burton | A61M 16/10 128/204.23 |
| 2005/0267362 A1 | 12/2005 | Mietus | |
| 2006/0011198 A1 | 1/2006 | Matarasso | |
| 2006/0180149 A1 | 8/2006 | Matarasso | |
| 2007/0032733 A1 | 2/2007 | Burton | |
| 2007/0118054 A1 | 5/2007 | Pinhas | |
| 2007/0193583 A1 | 8/2007 | Reed | |
| 2007/0208269 A1 | 9/2007 | Mumford | |
| 2007/0215146 A1 | 9/2007 | Douglas | |
| 2007/0221224 A1 | 9/2007 | Pittman | |
| 2008/0066753 A1 | 3/2008 | Martin | |
| 2008/0078384 A1 | 4/2008 | Messenger | |
| 2008/0127978 A1 | 6/2008 | Rubin | |
| 2010/0049008 A1 | 2/2010 | Doherty | |
| 2010/0152543 A1 | 6/2010 | Heneghan | |
| 2010/0179613 A1 | 7/2010 | Stahmann | |
| 2011/0132378 A1 | 6/2011 | Levendowski | |
| 2011/0137197 A1 | 6/2011 | Stahmann | |
| 2011/0178377 A1 | 7/2011 | Heneghan | |
| 2011/0192400 A9 | 8/2011 | Burton | |
| 2011/0203588 A1* | 8/2011 | Armitstead | A61M 16/0003 128/204.21 |
| 2012/0179061 A1 | 7/2012 | Ramanan | |
| 2014/0137870 A1 | 5/2014 | Barlow | |
| 2015/0031964 A1 | 1/2015 | Bly | |
| 2016/0125160 A1 | 5/2016 | Heneghan | |

* cited by examiner

METHODS AND APPARATUS FOR ASSESSING SLEEP QUALITY

CROSS-REFERENCE TO RELATED APPLICATIONS

This application is a continuation application of U.S. application Ser. No. 14/085,327, filed Nov. 20, 2013, now allowed; which is a continuation of U.S. application Ser. No. 12/311,361, filed on Oct. 6, 2009, now U.S. Pat. No. 8,617,068; which claims benefit to PCT Application No. PCT/AU2007/001440, filed on Sep. 27, 2007, and Australian Provisional Patent Application No. 2006905343, filed on Sep. 27, 2006, the entire contents of which are hereby incorporated herein by reference.

FIELD OF THE INVENTION

The exemplary embodiments disclosed herein relate to methods and apparatus for treatment of sleep disorders, including, for example, sleep disordered breathing (SDB), and for assessment and communication of sleep quality.

BACKGROUND OF THE INVENTION

Excessive daytime sleepiness (EDS) is widespread throughout the population, interfering with day-to-day activities, work, and relationships. EDS reduces productivity, concentration, memory, and can negatively impact on mood, and may cause danger to the community by those affected driving or operating machinery while drowsy.

Daytime sleepiness may be caused by an underlying medical condition such as sleep disordered breathing, by insufficient sleep resulting from poor sleep hygiene, self-imposed or socially dictated sleep deprivation, etc.

There have been attempts to quantify sleepiness, or to assess sleep quality.

Introspective behavioral scales and performance tests have been used to measure sleepiness and use subjective scales to query the individual's perception of alertness/sleepiness.

The Stanford sleepiness scale and Karolinska Sleepiness Scale assess the momentary degree of alertness/sleepiness. This is useful for a period but generally is less helpful in examining the global feelings of sleepiness. Also, in order to achieve accurate results, a subjective evaluation that is representative of the entire period between treatment sessions is needed.

The Epworth sleepiness scale (ESS) is a self-administered questionnaire used to determine the subject's general level of daytime sleepiness. Participants are asked to rate the likelihood that they would fall asleep in a range of common everyday situations. A rating of 0 means that the subject would never fall asleep compared to 3, meaning there is a high chance of dozing or falling asleep.

The summation of these ratings is the ESS score—an Epworth score of 0 is non-sleepy, 10 or more is considered sleepy, and 18 or more is very sleepy.

The Pittsburgh Sleep Quality Index (PSQI) is another method for determining sleep quality and sleep disturbances. The PSQI is a self-rated questionnaire which assesses sleep quality and disturbances over a 1-month time interval. Nineteen individual items generate seven "component" scores: subjective sleep quality, sleep latency, sleep duration, habitual sleep efficiency, sleep disturbances, use of sleeping medication, and daytime dysfunction. The sum of scores for these seven components yields one global score. The higher scores generally correlated with greater sleep complaints and therefore diminished quality.

Another new method of measuring perceived sleepiness is to use pictorial scales which depict cartoon pictures of different degrees of tiredness.

Objective tests to measure sleepiness include Pupillography, the Multiple Sleep Latency Test (MLST), and Maintenance of Wakeful test.

Pupillography is based on changes in pupil stability that corresponds to the level of alertness. This technology is currently used in devices that are designed to prevent driver fatigue.

The Multiple Sleep Latency Test (MSLT) provides a valid measure of daytime sleepiness on the particular day of the test. This test is based on the premise that the sleepier the subject, the faster they will fall asleep when encouraged to do so while lying down in a non-stimulating environment (Johns 1991). The MSLT includes four to five opportunities to nap spaced across the day at 2-hour intervals. The MSLT is very cumbersome, time consuming, and expensive to perform, as it takes all day.

The Maintenance of Wakeful test is similar to the MSLT and asks patients to try to remain awake for as long as possible. It is currently used for legal purposes to determine if someone suffers from excessive daytime sleepiness.

However, for these methods to be useful tools for improving the patient's sleep, the patient must have insight into the problem and be able to distinguish between sleepiness from other factors affecting performance.

There have also been objective measurements of the patient's sleep quality.

In U.S. Publication No. 2005/0267362, an assessment of sleep quality and sleep disordered breathing is determined from cardiopulmonary coupling between two physiological data series—an R-R interval series derived from an electrocardiogram (ECG) signal, and an ECG-derived respiration signal.

In U.S. Pat. No. 6,120,441 (Griebel), various sensors detect a patient's body functions which are stored in a recorder. The stored data is then transferred to a computer where it is analyzed and evaluated.

U.S. Pat. No. 6,468,234 (Van der Loos et al.) describes a method and apparatus for measuring sleep quality that utilizes sensors incorporated in a sheet which is laid on top of a conventional mattress on which the subject sleeps, interface software for collecting user lifestyle data, and lifestyle correlation software for correlating the lifestyle data with the data acquired by said array of sensors.

U.S. Pat. No. 6,878,121 (Krausman et al.) describes a device which uses a motion sensor to measure the movement of a patients arm during sleep and then produces a sleep score based on these movements.

However, the existing arrangements can be improved upon in terms of sufficiency of measurement and feedback to the patient regarding their sleep.

SUMMARY OF THE INVENTION

In certain example embodiments, a method of assessing sleep quality of a patient in a sleep session is provided. Sleep session data comprising two or more measured physiological parameters of the patient which are indicative of the patient's sleep quality during the sleep session is obtained. A composite sleep quality index is calculated from said two or more sleep session data parameters (e.g., determined over a period comprising two or more sleep sessions). The composite sleep quality index is communicated to the patient.

In certain other example embodiments, a method of assessing sleep quality of a patient in a sleep session is provided. Sleep session data comprising one or more measured physiological parameters of the patient which are indicative of the patient's sleep quality during the sleep session is obtained. A score index is derived from the sleep session data parameter and patient feedback data from previous sleep sessions (which may be electronically recorded). The score index is communicated to the patient.

In certain other example embodiments, a method of assessing sleep quality of a patient in a sleep session is provided. Sleep session data comprising one or more measured physiological parameters of the patient which are indicative of the patient's sleep quality during the sleep session is obtained (e.g., recorded and stored electronically). A score index is derived from the sleep session data parameter and patient profile data. The score index is communicated to the patient.

In certain other example embodiments, a method of assessing sleep quality of a patient in a sleep session is provided. Sleep session data comprising one or more measured physiological parameters of the patient which are indicative of the patient's sleep quality during the sleep session is obtained. A score index is derived from the sleep session data parameter and optimal sleep characteristics data for the patient. The score index is communicated to the patient.

In certain other example embodiments, a method of assessing sleep quality of a patient in a sleep session is provided. Sleep session data comprising two or more measured physiological parameters of the patient which are indicative of the patient's sleep quality during the sleep session is obtained. Subjective patient feedback data is obtained. A composite sleep quality index is calculated using said sleep session data and said patient feedback data. The composite sleep quality index is communicated to the patient.

In certain other example embodiments, an apparatus for assessing sleep quality of a subject, including apparatus for supplying breathable gas under pressure to the subject for treatment of sleep disordered breathing, is provided. One or more sensors is/are configured to measure sleep session data comprising a plurality of physiological parameters of the patient which are indicative of the patient's sleep quality during the sleep session. A processor is configured to calculate a composite sleep quality index from said two or more sleep session data parameters. A display is provided to communicate the composite sleep quality index to the patient.

In certain other example embodiments, a method of assessing sleep quality of a patient in a sleep session is provided. Sleep session data comprising one or more physiological parameters of the patient which are indicative of the patient's sleep quality during the sleep session is obtained. Subjective patient data is obtained. A calculation is applied to said sleep session data to calculate a sleep quality index indicative of the quality of the patient's sleep, said calculation being dependent on said subjective patient data. The sleep quality index is communicated to the patient.

In certain other example embodiments, a method of assessing sleep quality of a patient in a sleep session is provided. Sleep session data comprising one or more physiological parameters of the patient which are indicative of the patient's sleep quality during the sleep session is obtained. Subjective patient data is obtained. A calculation is applied to said sleep session data to calculate a sleep quality index indicative of the quality of the patient's sleep. The sleep quality index is communicated to the patient, including adapting the form of said communication dependent on said subjective patient data.

In certain other example embodiments, a method of assessing sleep quality of a patient whilst undergoing therapy for a sleep disorder is provided. Sleep session data comprising one or more physiological parameters of the patient which are indicative of the patient's sleep quality during a sleep session in which the patient undergoes said therapy is obtained. Feedback is communicated to the patient regarding patient's sleep quality during the sleep session, including providing information to the patient on improvements for future therapy sessions, said information being based on said sleep session quality for the sleep session.

The information may include, for example, directions for adjustment of therapy apparatus for future therapy sessions, such as adjustments to be made to the patient interface, or directions for modification to therapy settings for future therapy sessions.

In another example embodiment, a flow generator of a sleep disordered breathing treatment device is provided. The flow generator comprises a user interface having an adjustment device comprising a knob, one or more buttons, a lever, or the like, and a number of settings that correspond to sleep ratings (e.g., a good night's sleep, a bad night's sleep, tired, awake, etc.). The adjustment device is readily accessible on the flow generator for use by the patient. The adjustment device includes a first setting which transmits data to a control algorithm of the flow generator corresponding to the patient having slept well and a second setting which transmits data to the control algorithm corresponding to the patient having slept badly.

In certain example embodiments, a method of treating a patient for sleep disordered breathing including the use of a flow generator is provided. Sleep data comprising one or more physiological parameters of the patient indicative of the patient's sleep quality from a recording device over at least one sleep session is obtained. Observations from the patient after the at least one sleep session are obtained, with the observations being indicative of the quality of the patient's at least one sleep session. A composite sleep quality value is calculated from the one or more physiological parameters and the observations from the patient. A flow generator adjustment is calculated as a function of the composite sleep quality value. Parameters of the flow generator are adjusted in dependence on the calculated flow generator adjustment.

In certain example embodiments, a method of adjusting the treatment pressure regime of a sleep disordered breathing treatment device is provided. Observational data from a patient after one or more sleeps sessions is electronically recorded and stored, with the observational data being indicative of the quality of the patient's one or more sleeps sleep sessions. The sleep disordered breathing treatment device is adjusted on the basis of the observational data.

In certain example embodiments, an apparatus and/or system may be provided for carrying out the above methods. Furthermore, the various example aspects and/or example embodiments described herein may be used alone and/or in combination with other example aspects and/or example embodiments to realize yet further example embodiments.

For example, in certain example embodiments, a patient accessible input device is provided. A user interface is configured to receive a patient input from the patient corresponding to a perceived quality of sleep of the patient. A transmission device is configured to transmit the patient input to a processor configured to adjust one or more parameters of a flow generator of a sleep disordered breathing treatment device to optimize the treatment regime.

In certain example embodiments, a sleep disordered breathing treatment system is provided. A user interface is configured to receive a patient input from the patient corresponding to a perceived quality of sleep of the patient. A computer-readable storage device stores computer-executable process steps for altering one or more treatment algorithms. A processor is operatively connected to the user interface and the storage device. When a patient provides a patient input into the system via the user interface, the processor is configured to execute the computer-executable process steps by which the one or more treatment algorithms are adjusted according to the patient input.

In certain example embodiments, there is provided an automatically adjusting flow generator comprising a user interface configured to receive a patient's assessment of how well the patient has slept, with the flow generator being configured to adjust its control algorithm in response to the patient's assessment to optimize therapy.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

1. The Sleep Cycle

Sleep is best distinguished from quiet waking by changes in neuronal activity patterns—as manifested in electroencephalogram (EEG) readings—and by loss of behavioral responsiveness.

The sleep cycle of a healthy sleep structure can be divided into the two principle segments of Rapid Eye Movement (REM) sleep and Slow Wave Sleep (SWS). SWS sleep can then be further divided into four distinct phases, including stage 1, 2, 3, and 4, as illustrated in FIG. 1.

Figure 1:
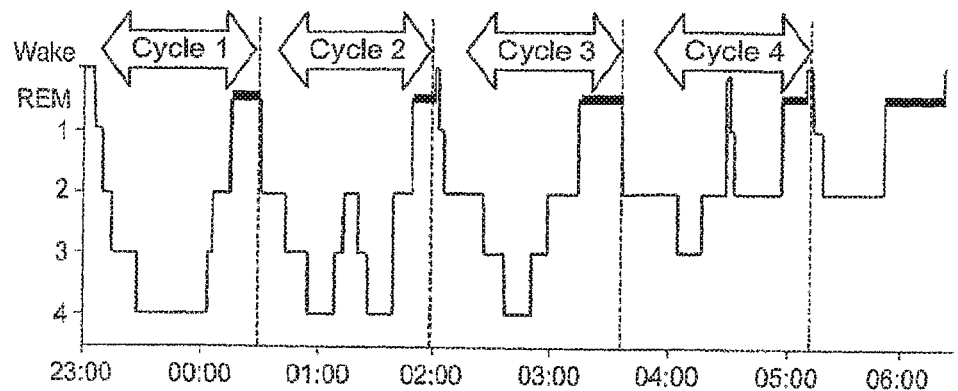
FIG. 1 illustrates the sleep cycle in healthy sleep.

As can be seen in FIG. 1, as a person sleeps, the person progresses through the different stages of sleep in a cyclic manner. Across the night, the average period of a total cycle is approximately 90-110 minutes. If the subject is aroused, the subject returns to the awake state and the cycle restarts.

Each stage has specific characteristics that are largely determined by measuring the electrical activity of the brain using an electroencephalogram (EEG) apparatus. The EEG measures brainwaves of different frequencies within the brain by placing electrodes on specific sites of the scalp.

The raw EEG data is usually described in terms of frequency bands: Gamma (>30 Hz), BETA (13-30 Hz), ALPHA (8-12 Hz), THETA (4-8 Hz), and DELTA (less than 4 Hz).

Detection of each stage of sleep from the EEG readings may be done by applying known criteria, such as those set out in "A Manual of Standardized Terminology, Techniques and Scoring System for Sleep Stages of Human Subjects" by Rechtschaffen and Kales (1968) and the proposed supplements and amendments (Psychiatry and Clinical Neurosciences 2001, 55, 305-310) (1996).

Figure 2:
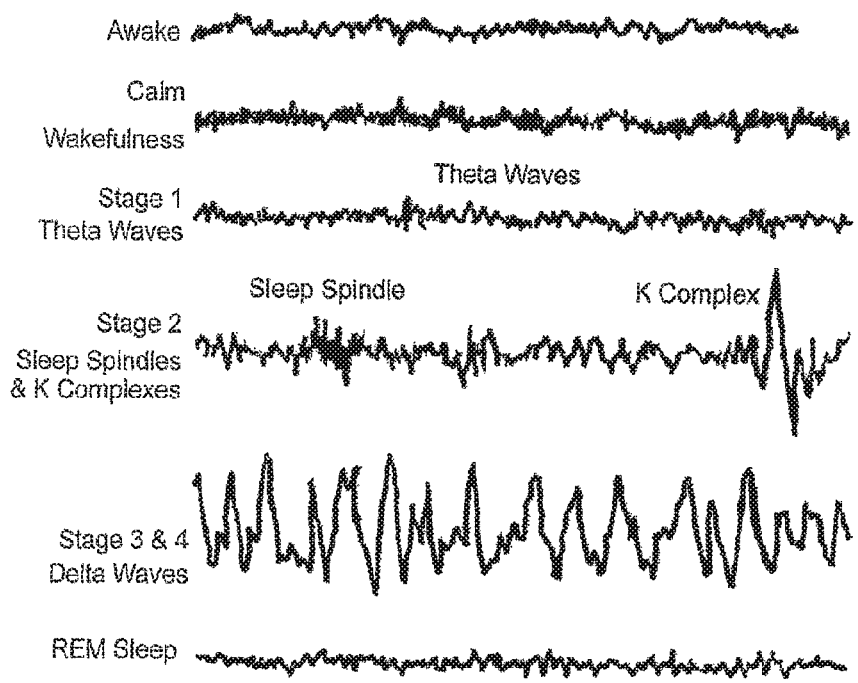
FIG. 2 illustrates characteristic EEG results for the different stages of sleep.

FIG. 2 shows typical EEG readings characteristics of each sleep stage.

The following is a brief outline of each of the sleep stages in healthy sleep.

1.1 Sleep Onset

Sleep onset is the first epoch scored as one of the standard sleep stages (1, 2, 3, 4, and REM) after the lights are darkened or the patient goes to bed.

1.2 Stage 1 Sleep

Stage one sleep is the transition between sleep and wakefulness and has the following characteristics. The EEG results indicative of stage 1 are largely in the alpha ranges with EEG vertex spikes. No sleep spindles or K-Complexes are present. The eyes often move in a slow rolling movement and at this stage the arousal threshold is low. Body movement is common during the transition from the wakeful stage to the sleep stages. Stage one generally lasts between 1 and 10 minutes and comprises 4-5% of total sleep time.

1.3 Stage 2 Sleep

Stage 2 is the next stage of sleep and has a higher arousal threshold than stage 1. The EEG indicators of stage two are predominantly theta waves with up to 20% of high voltage delta waves. EEG vertex spikes are common, as are sleep spindles with K complexes. The heart rate generally slows and the body temperature decreases. This stage can last up to 1 hour and comprises between 45-55% of total sleep time.

1.4 Stage 3 Sleep

Stage 3 is the beginning of deep sleep. It is characterized by high amplitude delta waves, specifically 20-50% of a 30 sec. period comprising EEG waves less then 2 Hz and more then 75 uV. It comprises between 4-6% of total sleep time and generally appears only in the first third of the total sleep period.

1.5 Stage 4 Sleep

Stage 4 is the deepest stage of sleep. It is characterized by high amplitude delta waves, the same as Stage 3, except 50% or more of each 30 sec. period comprises EEG waves less then 2 Hz and more the 75 uV. Stage 4 comprises 12-15% of total sleep and usually appears only in first third of sleep period. As this is the deepest stage of sleep, it has the highest arousal threshold.

1.6 Rapid Eye Movement (REM)

REM sleep is characterized by rapid eye movements and the paralysis of all postural muscles. EEG recordings are low-voltage, fast-frequency, non alpha, and usually comprise 20-25% of total sleep time. REM is well known for being the stage of sleep when dreaming occurs and is thus thought to be strongly linked to mental development and memory. Brain activity and metabolism is extensive, and there is extensive excitement of the central nervous system. The duration of REM sleep increases with each subsequent cycle of sleep

2. Characteristics of Quality Sleep

Insufficient or excess duration, significant fragmentation, and an incorrect sleep structure are significant causes of disrupting or inhibiting the essential processes that occur during sleep.

2.1 Duration

It is vital that the patient receives the correct duration of sleep. Both insufficient and excessive sleep duration may have detrimental health effects.

There are differing opinions as to the optimum duration of sleep. The widely held belief is that adults require at least 8 hours of sleep per night to not suffer the effects of sleep deprivation and to remain healthy. Some studies have suggested 7 hours is optimal, while other theories suggest that people's sleep need declines with age from a maximum when we are first born, 16 hours, reducing almost linearly to about 6.5 hours at the age of 70.

Sleeping for less than the optimal duration will cause sleep deprivation, while sleeping longer than optimal can cause sleep problems by reducing the drive to sleep and thus reducing sleep efficiency.

Optimum sleep duration appears to be a very individual reading. Many researchers believe there may be unknown biological and genetic factors affecting people's required sleep duration, in addition to age, sex, and lifestyle demographics. Hence, there is an inter-individual variability which precludes generalizations.

In one example embodiment, a determination of a patient's optimum sleep duration starts with the outer bounds of 6-9 hours, or with a starting point within that range, and then over time isolates the duration, specific to each patient, based on an experience algorithm that correlates the level of daytime sleepiness and actual sleep duration to determine the optimal duration.

2.2 Fragmentation

There is increasing agreement that the essence of quality sleep is continuity and that fragmentation seriously inhibits the essential processes that occur during sleep. This factor is often unrecognized by the patient as a cause of poor sleep because the subject does not remember the arousals, and thus patients are often unaware that their sleep has been fragmented and accordingly extremely inefficient.

However, not all arousals should be considered as being disruptive to sleep. All subjects appear to have a certain number of spontaneous arousals which are an intrinsic component of physiological sleep and which may still be considered to constitute undisturbed sleep.

Excessive fragmentation can result in significantly altered distribution of sleep stages, the appearance of subjective daytime sleepiness, and objective performance decrement.

Abnormal fragmentation does lead to the disruption of the sleep process and inhibits the essential processes that occur during sleep.

According to the American Sleep Disorder Association (ASDA) "arousals are characterized by abrupt changes in EEG frequency, which may include theta, alpha and/or frequencies greater than 16 Hz but not spindles. At least 10 seconds of continuous sleep must precede the EEG arousal, and a minimum of 10 seconds of intervening sleep is necessary to score a second arousal.

An excessive number of arousals will also disrupt the sleep structure of the subject.

2.3 Sleep Structure

As previously stated, having the correct sleep structure is a characteristic of quality sleep. Each stage of sleep is hypothesized to serve a specific purpose and, therefore, if one stage is reduced or even eliminated then this will interfere with the specific functions that occur during that stage. Conditions such as depression, narcolepsy, and sleep apnea are all characterized by having abnormal sleep structures.

Total sleep time should comprise 4-5% of stage 1, 45-55% of stage 2, 4-6% of stage 3, 12-15% of stage 4, and 20-25% of REM. However there are some external factors that influence sleep structure, and the impact of these factors often depends what sleep cycle it is. As sleep progresses, the percentage of REM increases and the duration of stage 3 and 4 declines.

Figure 3:
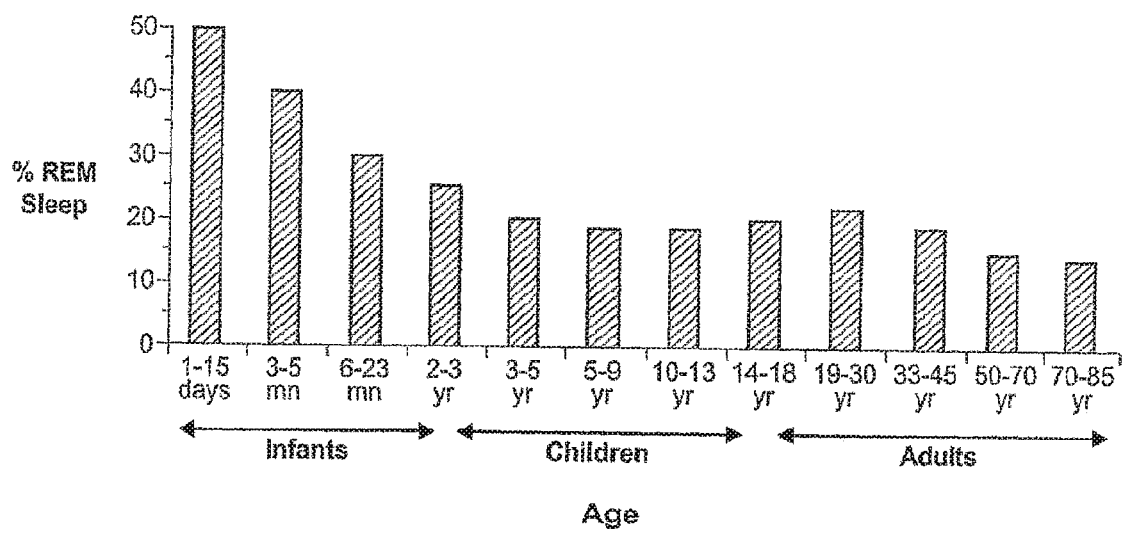
FIG. 3 is a graph showing the change in the proportion of REM sleep with age.

Age also significantly affects sleep structure as demonstrated by FIG. 3. REM sleep is highest during infancy and early childhood, drops off during adolescence and young adulthood, and decreases further in older age. Stages 3 and 4 in the first sleep cycle shorten even more dramatically in older people than they do during a typical night for everyone else, so older people get less total deep sleep than younger people. Also with age comes the lengthening of the first REM stage.

The optimum sleep structure for each individual patient generally will be similar to the optimum duration in that it will be specific to each person yet most usually within the normal bounds as listed above. To determine the optimum sleep structure, a similar method to duration may also be used, e.g., start with an assumed optimal sleep structure within normal bounds and apply an adaptive algorithm to determine which sleep structure corresponds to the minimal level of daytime sleepiness.

3. Measurement of Physiological Data

Quantitative determination of physiological sleep session parameters—and the sleep quality parameters of sleep duration, fragmentation, and sleep structure—may be measured by the incorporation of an EEG sensor into positive airway pressure (PAP) and non-invasive ventilation (NIV) apparatus used for the treatment of sleep disordered breathing.

The EEG is a non-invasive method for determining brain activity. Brain activity causes electrical impulses. These electrical signals are measured through electrodes on the patient's scalp/forehead that are connected to galvanometers. As previously discussed, the different stages of sleep can be characterized by their signature EEG signals.

Modern EEGs have been reduced to a single channel and only three electrodes need now be placed below the hairline, as opposed to attaching the electrodes to the scalp as required in older EEG technology. Examples of EEG measurement apparatus suitable for use in the present embodiments include the BioSomnia Plus by Oxford BioSignals Limited of Oxford, UK.

The EEG electrodes may be incorporated into the soft components of the apparatus, such as the headgear, mask cushions, or nasal prongs. The data from the EEG sensors may be sent by wire running along the gas flow tube to a processor built into the flow generator for processing and analysis, or may be transmitted using wireless technology.

One alternative to the use of EEG for monitoring of the physiological data is the use of pulse plethysmographs (otherwise known as pulse oximetry), which may also provide other useful information on central nervous system activation.

Sensors and techniques which may be used to measure the patient's physiological sleep session data may include one or more of the following:

3.1 Duration-Related Sensors

Timer—the timer of the flow generator may be used to measure: time the machine is turned on to time it is turned off; time from the first apnea prevention to when it is turned off; time from first apnea prevention to time to last apnea prevention, etc.

EEG—as discussed above, an EEG apparatus may measure brainwaves to determine sleep onset and arousal and hence calculate duration.

Electromyography—may be used to detect muscle movement and therefore can detect arousal if arousal is defined by a movement threshold.

Electro-Oculogram—measures eye movement and hence can determine duration if it is assumed that the detection of slow eye movement determines the onset of sleep, to detect arousal from sleeping to wakefulness, etc.

Facial Recognition Sensors—may be used to detect sleep duration by changes in the patient's face between sleep and wakefulness.

Accelerometer—may be mounted on the patient to detect transition from wakefulness to sleep by noting a change in the level of movement of the patient.

Pulse oximeter—measures pulse and also blood oxygen levels. Different pulse rates may mark the difference between resting and awake, optionally used in conjunction with other sensors to validate results.

3.2 Fragmentation-Related Sensors

Accelerometer—as discussed above, may be used to measure movement and hence detect arousal accompanied by movement.

EEG—may measure brainwaves to determine sleep onset and arousal and hence calculate fragmentation.

Pressure and flow sensors, such as those used in current flow generator technology, may be used to determine apneas and hence detect arousals.

3.3 Sleep Structure Related Sensors

Electro-Oculogram—may be used to detect rapid eye movement sleep.

Facial Recognition—may detect REM, where resolution is high enough to detect eye movement.

Accelerometer—measures movement and detects REM sleep by the lack of movement, as no movement occurs during REM sleep.

Pulse oximeter—measures pulse and also blood oxygen levels. Different heart rates may correspond to different stages in sleep, optionally with correlation to other sensor results.

Also, currently known techniques to monitor apneas may be used, with correlation between the number of times the device has to prevent an apnea and the stage of sleep.

3.4 AHI

Currently known techniques for measuring AHI may be used. Alternatively, or additionally, AHI may be detected from a combination of sleep structure and fragmentation techniques described above, with an AHI event being inferred from an arousal or by an unexpected transition from one sleep state to another.

3.5 Sleep Latency

The same techniques mentioned above for duration may be used, except with the sleep latency measurement being taken from the time the machine is turned on to the time it is registered that the patient is sleeping, or optionally from the time that the patient indicates he or she is attempting to sleep, if the patient is reading, etc., prior to attempting to sleep.

3.6 Snore Results

Microphone—recognition of snoring by microphone is advantageous in that it is applicable for patients who are not using flow generator.

Pressure and flow sensors—snore measurement utilizing current flow generator techniques may be used.

4. Collecting Patient Feedback Data

The patient may be quizzed at the end of each sleep session, at a predetermined time during the day, and/or before commencement of the next session, to provide subjective data concerning sleep quality and sleepiness. This feedback may conveniently be collected using the graphical interface and controls of the flow generator, or alternatively via a communication link to a separate interface device such as the Health Buddy device manufactured by Health Hero Network, Inc. of Mountain View, Calif., USA. The questions may, for example, be similar to those used in the Epworth Sleepiness Scale.

5. Calculating the Overall Sleep Quality Index

Figure 4:
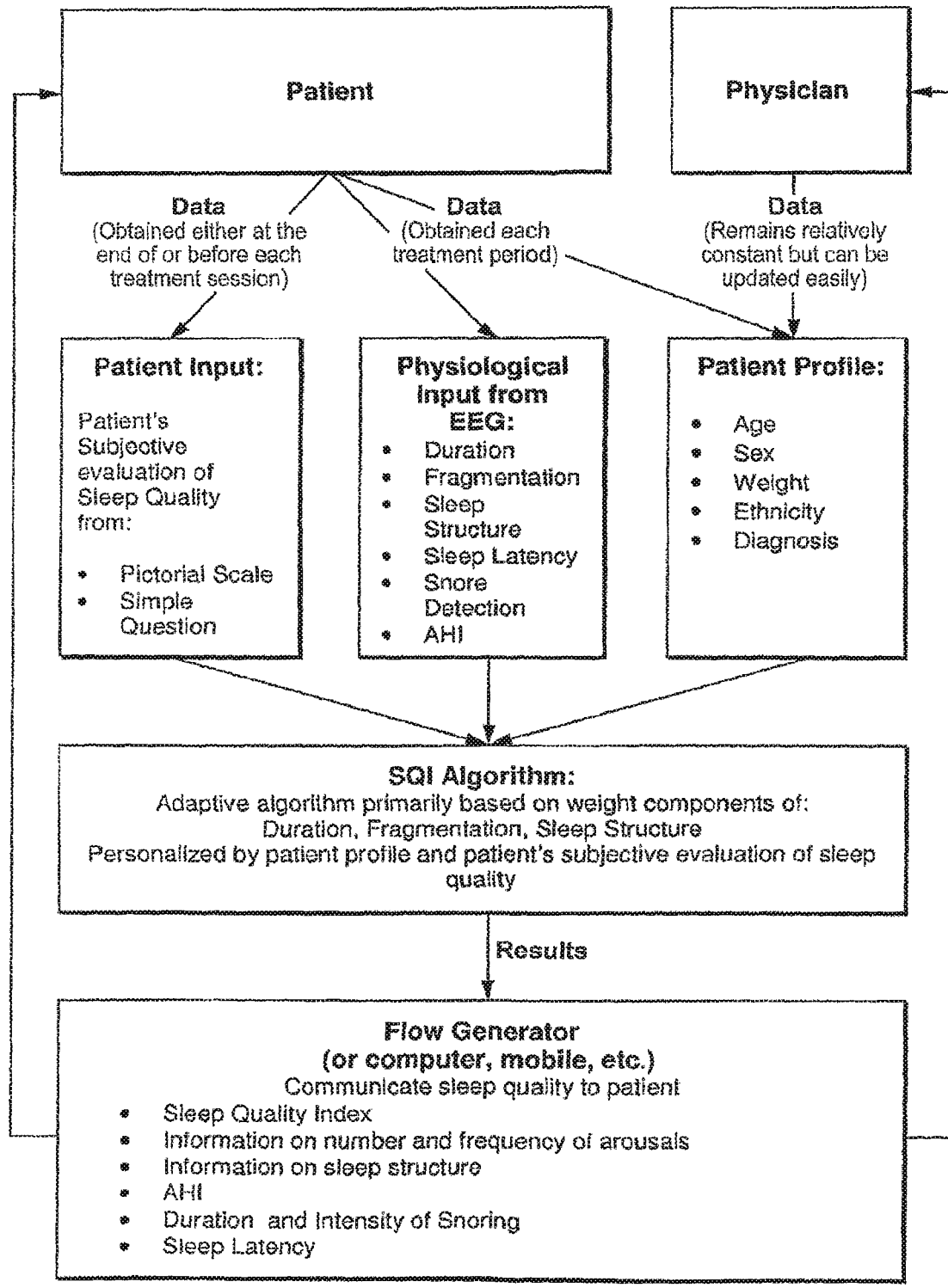
FIG. 4 is an overview of calculation of a sleep quality index in accordance with an example embodiment.

FIG. 4 is an overview of the calculation of a composite sleep quality index (SQI) according an example embodiment.

As a first step, the patient's physician programs the patient's profile data—e.g., data that will remain relatively static over numerous treatment sessions, such as, for example, age, sex, weight, ethnicity, and severity of diagnosed sleep disordered breathing—into the CPAP flow generator. This programming may be done at the physician's premises or remotely by a communications link such as a modem line or other suitable network connection.

The sleep session physiological data from the EEG is collected while the patient sleeps and is stored in the processor or a computer-readable storage medium (e.g., a memory, disk drive device, smart card, etc.) of the flow generator. This physiological data forms the basis of calculation of a composite sleep quality index score.

In calculating the sleep quality score according to an example embodiment, the following parameters may used: duration, fragmentation, sleep structure, AHI, sleep latency, and/or snore results.

Generally, duration, fragmentation, and sleep structure will give the best indication of sleep quality. However, sleep quality could be determined on the basis of any one of the parameters alone.

Each parameter is given a score based on their value compared to an optimal value for that patient. Initially, the optimal values against which the individual parameters are scored will be determined primarily by the normal population results, as modified by the patient profile data. The scores set out in the tables below for each parameter are estimated. Also, sample scores are set out in the series of tables below.

5.1 Duration

The optimum duration may initially be set at 8 hours. However, this may be altered as the algorithm learns the optimum duration for the individual patient.

| Duration | Score | Rank |
| --- | --- | --- |
| Optimum less 2+ hours | 0 | 6 |
| Optimum less (2-1) hours | 3 | 5 |
| Optimum less (1-0) hours | 6 | 4 |
| Optimum | 10 | 1 |

-continued

| Duration | Score | Rank |
|---|---|---|
| Optimum + (0-1) hours | 9 | 2 |
| Optimum + (1-2) hours | 7 | 3 |

5.2 Structure

| Structure | Score |
|---|---|
| Insufficient REM sleep | 5 |
| Insufficient Stage 3 & 4 | 5 |
| Optimum | 10 |

5.3 Fragmentation

Excessive fragmentation decreases the quality of sleep and can be thought to have the same effect as decreased duration. Hence, in the present example, fragmentation affects the value of duration that is used in the quality calculations. The patient's age should be taken into account here, for example, as the average number of arousals that is acceptable increases with age.

| Fragmentation | New Value for Duration |
|---|---|
| >60 per hour | 0.4 * Duration |
| 31-59 per hour | 0.6 * Duration |
| 21-30 per hour | 0.85 * Duration |
| 15-20 per hour | 0.9 * Duration |
| 10-14 per hour | Duration |
| 5-9 per hour | Duration |
| 0-4 per hour | Duration |

5.4 Sleep Latency

Sleep latency is the time it takes to get to get to sleep. The time to fall asleep that is considered to be normal is about 15 minutes. The starting point for measurement of sleep latency may be the commencement of PAP treatment, or alternatively some other signal may be used, for example, having the patient press a button on the flow generator control panel.

| Sleep Latency Time | Score |
|---|---|
| >1.5 hours | 0 |
| 1-1.5 hours | 2 |
| 45-1 minutes | 4 |
| 30-45 minutes | 6 |
| 15-30 minutes | 8 |
| 0-15 minutes | 10 |

5.5 AHI

The apnea hypopnea index (AHI) is the number of apneas or hypopneas that a patient suffers per hour. Generally, an AHI of greater than 5 is believed to indicate sleep apnea.

| AHI | Score |
|---|---|
| 0-5 | 10 |
| 5-20 | 7 |
| 21-50 | 4 |
| >51 | 0 |

5.6 Snore

The snore parameter is a measurement of the number of times a patient snores throughout the treatment period. In order to ensure that speaking and other activities are not falsely recorded as snoring, the EEG may be required to register that a patient is asleep before detecting snore.

| Occurrence of Snoring | Score |
|---|---|
| 0-5 | 10 |
| 6-10 | 7.5 |
| 11-15 | 5 |
| 16-20 | 2.5 |
| >21 | 0 |

Other parameters which may be measured as indicators of sleep quality include heart rate, blood oxygen saturation, skin temperature, movement, respiration rate, muscle tone/tension, etc.

5.7 Total Calculation

The above measured scores are weighted according to relative importance to sleep quality and tallied to give a total sleep quality index score, for example, out of a total of 100.

In one example of the calculation:

$$\text{Sleep Quality Index} = (\text{Fragmentation Altered Duration}) * A + \text{AHI} * B + \text{Structure} * C + \text{Snore} + \text{Latency}$$

It should be noted that the weightings A, B, and C are adjustable. In one typical example: A=4, B=2, and C=2. Of course, it will be appreciated that the formula and weightings are presented by way of example and without limitation.

5.8 Adaptation of Sleep Quality Scores and/or Weighting

As the patient's treatment continues, the optimal values for calculation of the scores for the measured sleep session parameters may be modified by correlation of the subjective data results against the physiological data for the previous sleep session or sessions, as the system evolves to "learn" the exact criteria that corresponds to healthy sleep for the individual patient. For example, if it becomes apparent that the patient feels best the next day after 7 hours sleep rather than 8 hours, the duration scores will be modified to set 7 hours as the optimal duration for that patient.

Alternatively, or additionally, if the subjective feedback results show that the patient is unusually tolerant of arousals, or of disrupted sleep structure while still feeling refreshed the next day, the amount by which the fragmentation discounts the duration may be reduced.

Still further, if the correlation of the measured data and feedback data shows that the patient is particularly tolerant, or intolerant, of one of the component factors discussed above, the weighting of that parameter in calculation of the sleep quality index may be modified accordingly. Thus, it will be appreciated that in certain example embodiments, the calculation of sleep quality scores may be adjusted over time by varying the relative weightings and/or presence of certain variables.

6. Display of Results

The sleep quality index results may be communicated in any suitable manner to the patient, for example, graphically or audibly. For example, in an example embodiment, the results may be displayed graphically on the display of the flow generator, e.g., they may be called up as part of the menu structure of the machine.

The results may also be able to be downloaded to media or sent electronically by email or similar mechanisms to the patient's or clinician's computer. Where the patient's employment is safety-critical, for example, such as for long distance drivers or pilots, information may be sent to the employer's computer.

The sleep quality index may be displayed in any form which will be readily understood by the patient, for example, as a score out of 10 or 100, or as a rating out of 5 stars, as a graph, a row of lights, as different colors, etc.

The display may include a display of the individual sleep parameter measurements and/or their scores, as well as of the composite sleep quality index value, however displayed. Also, the display may allow a comparison of the sleep quality index values and/or the individual parameters across a range of sleep sessions or over a longer timeframe, for example, by the use of graphs.

The processor may also be configured to extrapolate using improvements to the patient's sleep quality index, for example, to show what effect any lifestyle and/or sleep hygiene changes (e.g., improvements or neglect, for example) are having on average life span, health statistics, likely work or sports performance, etc.

The sleep quality index may be used as a tool to teach patients to improve their sleep hygiene therefore enabling sleep disorder treatment to provide better results, the overall result being to involve patients in their treatment and to give them a sense of ownership and empowerment over their own treatment.

By providing the patient with an indicator of his or her sleep health which is meaningful to the patient, it is expected that there will be an increase in compliance with therapy related to educating and involving patients in their treatment and assisting the patients through the difficult adoption period where there is currently a high drop out rate. Similarly, it is expected that an apparatus incorporating the SQI will be useful as a tool to encourage and educate users, dynamically communicating the significant benefits of treatment and allowing patients, clinicians, partners, and caregivers to clearly see how the sleep and overall health has improved since the start of treatment.

By providing substantial real-time feedback that indicates how health and lifestyle changes are affecting their body and sleep patterns, the SQI may also have the effect of encouraging patients to improve their overall health.

Figure 5:
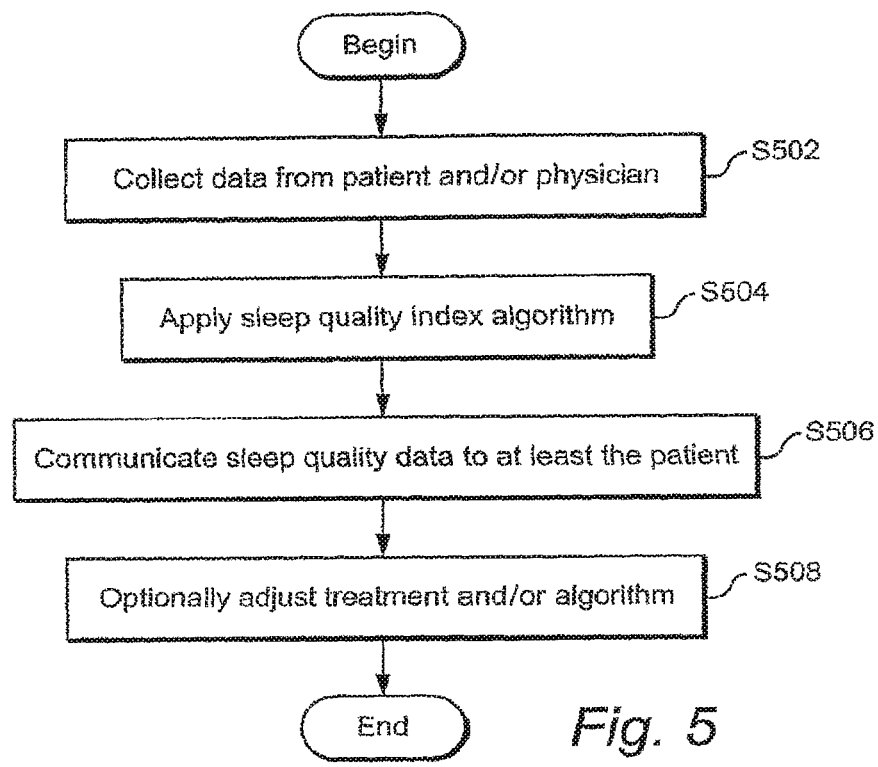
FIG. 5 is an illustrative flowchart showing a process for determining sleep quality index and communicating sleep quality data to at least a patient in accordance with an example embodiment.

FIG. 5 is an illustrative flowchart showing a process for determining sleep quality index and communicating sleep quality data to at least a patient in accordance with an example embodiment. Data is collected from the patient and/or physician in step S502. Such data may include, for example, sleep session data in the form of one or more physiological parameters of the patient indicative of the patient's sleep quality during the sleep session, a subjective evaluation of sleep quality made by the patient, etc.; patient profile data; and/or the like. The data may be input before and/or after a treatment session and/or a treatment regimen, etc. It may be gathered via manual input (e.g., to an interface located on or remote from the treatment device), automatically (e.g., from a treatment device substantially without direct user input), etc.

In step S504, a sleep quality index algorithm is applied. The sleep quality index algorithm may be an adaptive algorithm that takes into account some or all of the data collected in step S502. Sleep quality data may be presented to at least the patient in step S506. This sleep quality data may be displayed in any suitable format, e.g., a format useful for the patient to be appraised on the progress of the treatment, a format useful for a sleep clinician to monitor progress and/or assess the effectiveness of differing treatment regimens, etc. Optionally in step S508, the treatment and/or the algorithm may be adjusted, for example, based on the data. In this way, a patient also may be able to more concretely "see" the real effects of changes in treatment, lifestyle, etc.

Figure 6:
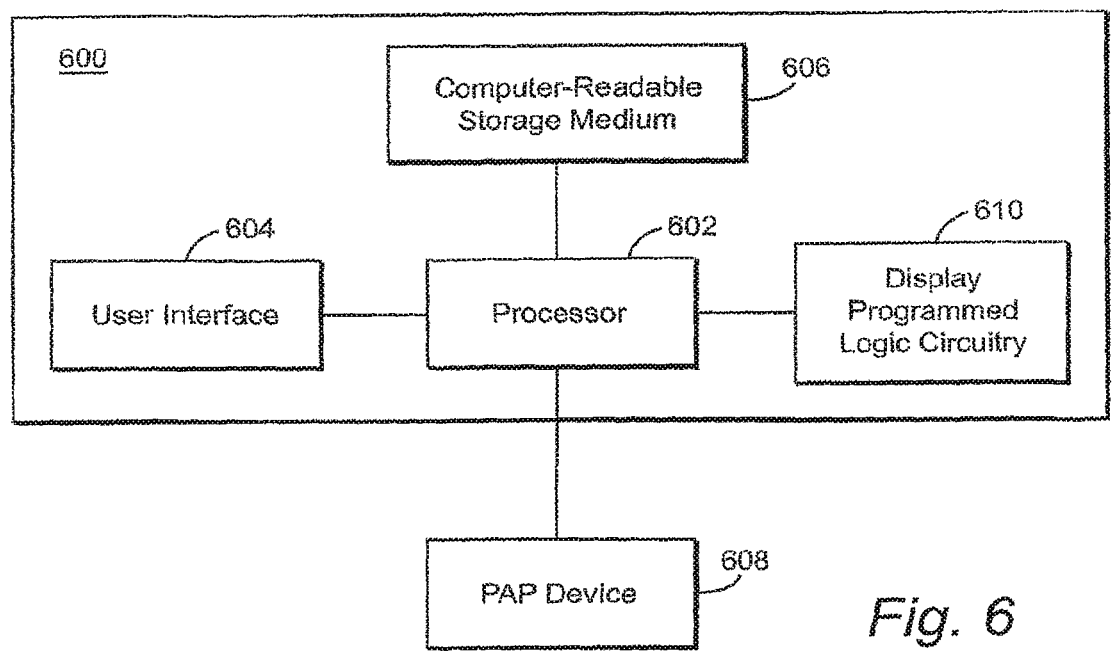
FIG. 6 is an illustrative block diagram showing an apparatus for determining sleep quality index and communicating sleep quality data to at least a patient in accordance with an example embodiment.

FIG. 6 is an illustrative block diagram showing an apparatus 600 for determining sleep quality index and communicating sleep quality data to at least a patient in accordance with an example embodiment. The apparatus 600 includes a processor 602. The processor 602 may receive input from a user interface 604 and/or a PAP device 608. This input may include, for example, sleep session data in the form of one or more physiological parameters of the patient indicative of the patient's sleep quality during the sleep session), a subjective evaluation of sleep quality made by the patient, etc.; patient profile data; etc. Optionally, the processor 602 may be configured to receive data from a remote source (e.g., via a transceiver, not shown in FIG. 6). The processor 602 may perform a calculation to arrive at a sleep quality index. To facilitate the storage of information and/or calculation of the sleep quality index, a computer-readable storage medium 606 (e.g., a memory, disk drive device, flash drive, smart card, etc.) may be provided to the apparatus 600. Display programmed logic circuitry 610 also may be provided to the apparatus 600 to display, for example, the sleep quality index, changes in the sleep quality index over time, interface screens in connection with the user interface 604, etc. The format of the display of information may be adjusted in dependence on user input in certain example embodiments. It will be appreciated that the above-described components may be implemented as any suitable arrangement of programmed logic circuitry (e.g., software, hardware, firmware, and/or the like, and/or any suitable combination thereof).

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments.

Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A method of assessing sleep quality of a patient in a sleep session, the method comprising:
   by way of a sensor, obtaining sleep session data comprising at least one physiological parameter of the patient indicative of the patient's sleep quality during a first sleep session in which the patient undergoes therapy;
   by way of a processor, processing the sleep session data to determine a first sleep quality index in which the patient undergoes said from said sleep session data;
   by way of the processor, extrapolating at least one patient characteristic based on a change to the first sleep quality index as compared to a prior sleep quality index, the at least one patient characteristic is not used to determine the first sleep quality index; and outputting the at least one patient characteristic on a display;

communicating feedback to the patient by displaying information on the display to the patient regarding improvements for future therapy sessions; and making adjustments to future therapy sessions based on the feedback provided to the patient; and wherein the at least one patient characteristic configured to provide data to the patient regarding effects of sleep hygiene and/or lifestyle changes.

2. The method of claim 1, wherein the at least one patient characteristic includes average expected life span, expected work performance, and/or expected athletic performance.

3. The method of claim 1, wherein the at least one physiological parameter includes sleep duration and sleep fragmentation.

4. The method of claim 1, further comprising prompting the patient to input subjective patient data into a user input, and processing, by way of the processor, subjective patient data, wherein the user input and the processor are in communication with one another, wherein the sleep session data and the subjective patient data together determine the first sleep quality index.

5. The method of claim 1, wherein the feedback to the patient is based on the first sleep quality index and, wherein said information being based on said sleep session quality for the first sleep session.

6. The method of claim 1, wherein said information includes directions for adjustment of a therapy apparatus for future therapy sessions.

7. The method of claim 6, wherein the directions for adjustment include steps to adjust a patient interface of the therapy apparatus.

8. The method of claim 1, wherein said information includes directions for modification to therapy settings for future therapy sessions.

9. The method of claim 8, wherein the directions for adjustment include steps to actuate one or more knobs, buttons, and/or levers on a flow generator in order to adjust the therapy settings.

10. The method of claim 1, further comprising:

obtaining patient profile data and processing, by way of the processor, the patient profile data;

wherein the sleep session data and the patient profile data together determine the first sleep quality index; and wherein the patient profile data includes at least one of patient age, sex, weight, ethnicity, and sleep disorder data.

11. The method of claim 1, further comprising:

prompting the patient to input subjective patient data into a user input, and processing, by way of the processor, subjective patient data;

wherein the user input and the processor are in communication with one another;

wherein the sleep session data and the subjective patient data together determine the first sleep quality index; and wherein the at least one physiological parameter includes sleep duration and sleep fragmentation.

12. An apparatus for assessing sleep quality of a patient while undergoing therapy for a sleep disorder, comprising:

a PAP device configured to supply breathable gas under pressure to the patient for treatment of sleep disordered breathing;

at least one sensor configured to obtain first sleep session data during a first sleep session in which the patient undergoes said therapy, said first sleep session data comprising at least one physiological parameter of the patient indicative of the patient's sleep quality during the first sleep session; and a processor configured to:

process the first sleep session data to determine a first sleep quality index indicative of the patient's sleep quality during the first sleep session, extrapolate at least one patient characteristic based on the first sleep quality index, output the at least one patient characteristic on a display;

communicate feedback to the patient by displaying information on the display to the patient regarding improvements for future therapy sessions; and adjust parameter of treatment of said PAP device based on the feedback provided to the patient;

wherein the at least one patient characteristic configured to provide data to the patient regarding effects of sleep hygiene changes.

13. The apparatus of claim 12, wherein the at least one patient characteristic includes average expected lifespan, expected work performance, and/or expected athletic performance.

14. The apparatus of claim 12, wherein the at least one physiological parameter includes sleep duration and sleep fragmentation.

15. The apparatus of claim 12, wherein the feedback to the patient is based on the first sleep quality index, and wherein said information being based on said sleep session quality for the first sleep session.

16. The apparatus of claim 12, wherein said feedback is configured to include directions for adjustment of a therapy apparatus for future therapy sessions.

17. The apparatus of claim 16, wherein the directions for adjustment are configured to include steps to adjust a patient interface of the therapy apparatus.

18. The apparatus of claim 12, wherein said information is configured to include directions for modification to therapy settings for future therapy sessions.

19. The apparatus of claim 18, wherein the directions for adjustment are configured to include steps to actuate one or more knobs, buttons, and/or levers on a flow generator.

20. The apparatus of claim 12, wherein the processor is further configured to prompt the patient to input subjective patient data into a user input, and process the subjective patient data, wherein the user input and the processor are in communication with one another, and wherein the first sleep quality index is a first composite sleep quality index made up of the first sleep session data and the subjective patient data.

* * * * *